United States Patent [19]
Hirai et al.

[11] 4,000,506
[45] Dec. 28, 1976

[54] BIPOLAR TRANSISTOR CIRCUIT

[75] Inventors: Susumu Hirai; Kunizo Suzuki; Hajime Yagi, all of Tokyo, Japan

[73] Assignee: Sony Corporation, Tokyo, Japan

[22] Filed: Apr. 9, 1975

[21] Appl. No.: 566,259

[30] Foreign Application Priority Data

Apr. 10, 1974 Japan ............................ 49-41464
May 10, 1974 Japan ............................ 49-52121

[52] U.S. Cl. .............................. 357/34; 357/14; 357/16; 357/58; 357/90
[51] Int. Cl.² ........................................ H01L 29/72
[58] Field of Search ............... 357/14, 16, 34, 58, 357/90

[56] References Cited
UNITED STATES PATENTS

| | | | |
|---|---|---|---|
| 2,822,310 | 2/1958 | Stieltjes et al. | 357/34 |
| 3,591,430 | 7/1971 | Schlegel | 357/34 |
| 3,761,319 | 9/1973 | Shannon | 357/34 |

OTHER PUBLICATIONS

H. Kroemer, "Theory of Wide–Gap Emitter For Transistors," Proc. Ire, vol. 45, No. 11, pp. 1535-1537, TK570017, Nov. 1957.

Primary Examiner—Andrew J. James
Assistant Examiner—Joseph E. Clawson, Jr.
Attorney, Agent, or Firm—Hill, Gross, Simpson, Van Santen, Steadman, Chiara & Simpson

[57] ABSTRACT

A transistor circuit comprising a bipolar transistor with high input impedance is disclosed. The transistor has low emitter-base conductance, and especially has a low conductance component caused by the recombination of minority carriers in an emitter. The emitter capacitance caused by stored minority carriers is low because of the low conductance component. These enable emitter-grounded operation at high current gain and high frequency.

5 Claims, 5 Drawing Figures

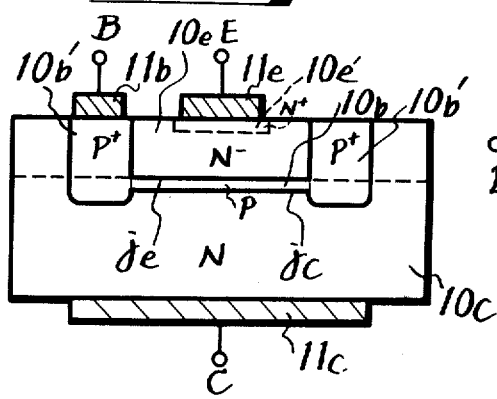
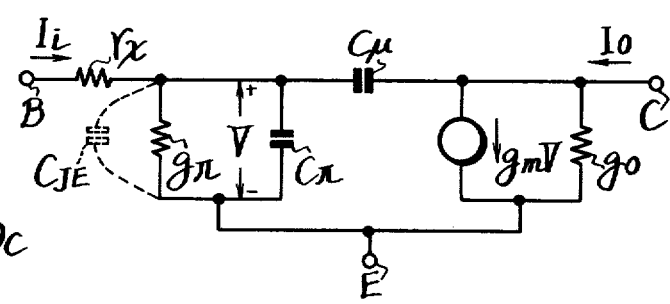
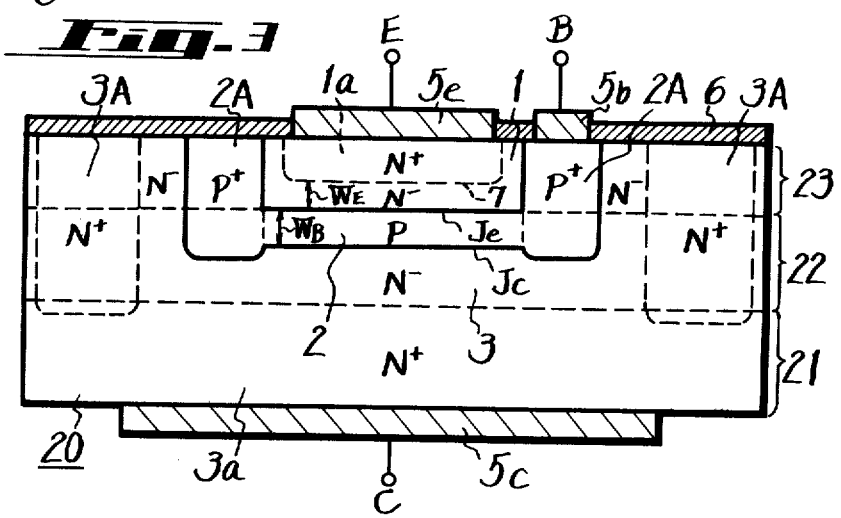
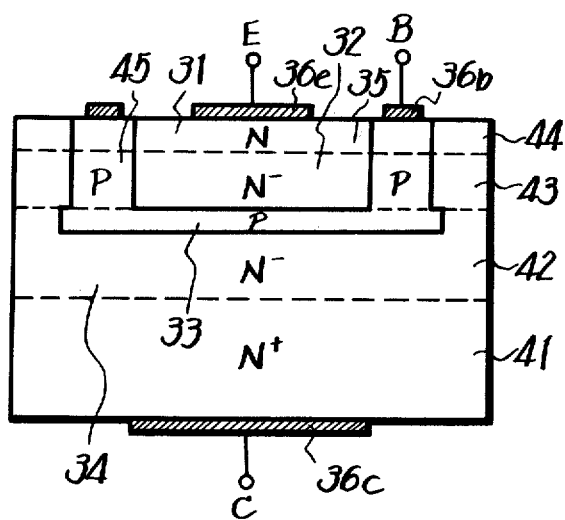
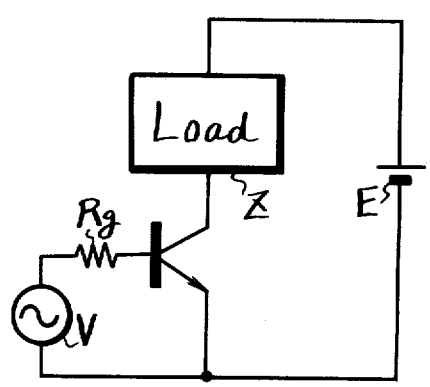

BIPOLAR TRANSISTOR CIRCUIT

BACKGROUND OF THE INVENTION

1. Field of the Invention

The present invention relates to a semiconductor circuit and particularly to a transistor circuit using a bipolar transistor with high input impedance.

2. Description of the Prior Art

A transistor having its base width greatly reduced in order to improve its high frequency characteristics is disclosed in U.S. Pat. No. 3,591,430.

The above mentioned transistor has such a construction as shown in FIG. 1, which illustrates an NPN-type transistor. In FIG. 1, an embedded base region 10b of, for example, P-type is formed on an N-type semiconductor substrate which is a collector region 10c, and a semiconductor layer forming an emitter region 10e is formed on the base region 10b. On the periphery of the embedded base region 10b there is formed a base electrode contact region 10b' of relatively high impurity concentration in an annular shape which is extended to the semiconductor surface. A base electrode 11b is deposited on the region 10b' in an ohmic contact therewith, an emitter electrode 11e is deposited on the emitter region 10e surrounded by the region 10b' in an ohmic contact therewith, and a collector electrode 11c is deposited on the collector region 10c in an ohmic contact therewith. Reference 10e' designates a region used to deposit the emitter electrode 11e on the emitter region 10e in ohmic contact therewith. Reference characters E, B and C indicate emitter, base and collector terminals, respectively.

In the thus constructed transistor, the portion of the base region facing the semiconductor surface, that is, the portion connected with the base electrode 11b, is formed therein as a region 10b' of relatively high impurity concentration, so that carrier injection is small relative to the surface of the aforesaid portion or relative to the lateral direction. For this reason, the emitter junction is operated mainly at a junction portion $j_e$ between the emitter region and the embedded region 10b, that is, a portion opposite a collector junction $j_c$. In addition, the thickness of the region 10b is quite small, so that the base transport factor $\beta$ is high.

Meanwhile, a consideration will be given on the emitter-grounded current amplification factor $h_{FE}$ which is used as one of parameters for evaluating the characteristics of a transistor. If the base-grounded current amplification factor is taken as $\alpha$, the emitter-grounded current amplification factor $h_{FE}$ is given as follows:

$$h_{FE} = \frac{\alpha}{1-\alpha} \tag{1}$$

Further, the base-grounded current amplification factor $\alpha$ is given as follows:

$$\alpha = \alpha^* \beta \gamma \tag{2}$$

where $\alpha^*$ is the collector amplification factor, $\beta$ is the base transport factor, and $\gamma$ is the emitter injection efficiency.

Considering now an emitter-grounded transistor circuit, a simplified hybrid $\pi$-type equivalent circuit for this circuit in a range between middle and high frequencies is shown in FIG. 2. In this circuit, the following letters or characters are employed:

| | |
|---|---|
| $r_x$: | base resistance, |
| $g\pi$: | parameter indicating recombination component of base current which is expressed as conductance for the sake of convenience in this specification, |
| $C\pi$: | parameter indicating component of base current corresponding to variation of excessively stored carriers, |
| $C\mu$, $g_o$: | Parameters indicating base width modulation according to collector voltage, |
| $g_m$: | mutual conductance, and |
| $C_{JK}$: | base-emitter junction capacity. |

In this case, if the variation of base current is taken as $i_b$ and the variation of emitter-base voltage as $v_{be}$, the parameters $g_\pi$ and $C_\pi$ are defined as follows:

$$i_b = g_\pi v_{be} + C_\pi \frac{dv_{be}}{dt} \tag{3}$$

On the other hand, the current amplification factor $h_{fe}$ of an AC component is defined by $h_{fe} = I_0/I_i$ in the case when an output is short-circuited, where $I_i$ is the input current and $I_0$ is the output current. Now, if the complex frequency is taken as $s$, a voltage V across $g_\pi$ and $C_\pi$ in FIG. 2 is expressed as follows:

$$V = \frac{I_i}{g_\pi + s(C_\pi + C_\mu + C_{JK})} \tag{4}$$

Further, since $I_0 = g_m V$ and normally $C_\mu << C_\pi$, the following relation is obtained:

$$h_{fe} \approx \frac{g_m}{g_\pi + s(C_\pi + C_{JK})} \tag{5}$$

Now, in an NPN-type transistor, $g_\pi$ is considered as being divided into a hole current component $g_p$ and an electron current component $g_n$ for the sake of convenience. That is, $$g_\pi = g_p + g_n \tag{6}$$

From the equations (5) and (6), the current amplification factor $h_{FE}$ of DC component or the current amplification factor at a time of $s = 0$ is expressed as follows:

$$h_{FE} = \frac{g_m}{g_\pi} = \frac{g_m}{g_p + g_n} \tag{7}$$

In the transistor shown in FIG. 1, since its base transport factor $\beta$ is made high as described previously, the recombination of electrons is small to satisfy the relation $g_n << g_p$. Accordingly, its $h_{FE}$ is given as follows:

$$h_{FE} \approx \frac{g_m}{g_p} \tag{8}$$

However, in normal transistors including the transistor of this kind, reducing the recombination of holes, is not considered so that $g_p$ is relatively large. For this reason, as apparent from the equation (8), relatively high $h_{FE}$ can not be obtained.

The conductance components $g_p$ and $g_n$ are expressed as follows. At first, emitter current $I_E$, collector current $I_C$ and base current $I_B$ are respectively given as follows:

$I_E = A(J_n + J_p)$
$I_C = \beta A J_n$
$I_B = I_E - I_C$
$I_B = A\{J_p + (1 - \beta)J_n\}$ where $A$ is junction area, $J_n$ is current density according to electrons injected from emitter into base, and $J_p$ is current density according to holes injected from base into emitter.

Further, the following relations are obtained:

$$g_p = A \frac{dJ_p}{dV} = A \frac{q}{kT} J_p$$

$$= \frac{1 - \gamma}{\beta \gamma} g_m$$

$$\approx (1 - \gamma) g_m \quad (9)$$

$$g_n = A(1 - \beta) \frac{dJ_n}{dV}$$

$$= A(1 - \beta) \frac{q}{kT} J_n$$

$$= \frac{1 - \beta}{\beta} g_m$$

$$\approx (1 - \beta) g_m \quad (10)$$

A transistor with its $J_p$ being reduced is disclosed in U.S. Pat. No. 2,822,310. In other words, the emitter is provided therein with a high resistive region whose thickness is selected smaller than the diffusion length of minority carriers thereby to reduce the current density $J_p$ according to the diffusion of minority carriers in this emitter.

In this connection, the emitter injection efficiency $\gamma$ is given as follows:

$$\gamma = \frac{J_n}{J_n + J_p} = \frac{1}{1 + \frac{J_p}{J_n}} \quad (11)$$

Accordingly, the reduction of $J_p$ is equivalent to the enhancement of $\gamma$.

SUMMARY OF THE INVENTION

It is a main object of this invention to provide a bipolar transistor circuit in which the cut-off frequency is high and the current amplification factor $h_{fe}$ in a range between intermediate and high frequencies is higher than those of the prior art embodiments mentioned above.

The other objects, features and advantages of the present invention will be apparent from the following description taken in conjunction with the accompanying drawing.

BRIEF DESCRIPTION OF THE DRAWING

FIG. 1 is a schematic enlarged cross-sectional view showing a prior art transistor, FIG. 2 is a hybrid $\pi$-type equivalent circuit of the prior art transistor shown in FIG. 1, FIG. 3 is a schematic enlarged cross-sectional view showing one example of a transistor according to this invention, FIG. 4 is a schematic enlarged cross-sectional view showing another example of a transistor according to this invention, and FIG. 5 is a circuit diagram showing an emitter-grounded type circuit using a transistor according to this invention.

DESCRIPTION OF THE PREFERRED EMBODIMENTS

A description will hereinafter be given of one embodiment of this invention with reference to FIG. 3. The illustrated example is of an NPN-type transistor, in which a semiconductor substrate 20 is provided therein with a first semiconductor region or emitter region 1 of first conductivity type, an N-type in this example, having high resistivity, a second semiconductor region or base region 2 of second conductivity type an P-type which is disposed adjacent thereto, and a third semiconductor region or collector region 3 of first conductivity type namely N-type having high resistivity which is disposed adjacent to the second region 2. A first PN-junction or emitter junction $J_e$ is formed between the first and second regions 1 and 2, and a second PN-junction or collector junction $J_c$ is formed between the second and third regions 2 and 3. In the example of FIG. 3, a high impurity concentration region 1a of the first conductivity type or N-type is provided in the first region spaced from junction $J_e$ by a distance $W_E$ to form an low-high impurity concentration junction 7(L–H) junction in the region 1, thus providing a potential barrier substantially parallel to and spaced from the emitter-base junction $J_e$ by a distance smaller than the diffusion length $L_p$ of minority carriers (holes) injected into the region which form the region 2 when the transistor is forwardly biased. By selecting a difference of impurity concentration sufficiently great between 1A and region 1, and by having the width of the high impurity concentration region 1A smaller than region 1, as hereinafter described, a potential barrier is obtained at 7 having an energy level higher than 0.1 eV and a built-in-field larger than $10^3$ V cm.

On the high impurity concentration region 1a of the first region, and the second and third regions 2 and 3, there are deposited first, second and third electrodes, that is, emitter, base and collector electrodes 5e, 5b and 5c, respectively, to lead out therefrom first, second and third terminals, that is, emitter, base and collector terminals E, B and C, respectively.

The manufacturing method of this semiconductor device will be described as follows. On an N-type semiconductor substrate 21 of high impurity concentration mainly forming a low resistive region 3a of the third region 3 there is epitaxially grown a semiconductor layer 22 of low impurity concentration forming the third region 3 of the same N-type. Then, on the semiconductor layer 22 there is selectively formed the second region 2 of P-type at a thickness of about $0.1\mu$ (micron) with the concentration in an order of about $10^{16}$ to $10^{18}$ atoms/cm$^3$ by diffusion or ion implantation. Next, on the semiconductor layer 22 there is epitaxially grown an N-type semiconductor layer 23 of low impurity concentration in an order of $10^{15}$ atoms/cm$^3$ at a thickness of about $0.2\mu$ which mainly forms therein the first region 1, thus the semiconductor substrate 20 being constructed. Then, a P-type impurity is selectively diffused across the semiconductor layer 23 in an annular shape with a relatively high impurity concentration in an order of $10^{20}$ atoms/cm$^3$ to form an extending region 2A which is used for leading out the electrode 5b for the second region 2. Next, the N-type region 1a of high impurity concentration in an order of about $10^{20}$ atoms/cm$^3$ is formed in the first region 1 with a thickness of about $0.1\mu$ by diffusion, for example, solid diffusion from the polycrystal semiconductor layer. Further, an extending portion 3A of the low resistive region 3a is formed outside the region 2A across the semiconductor layers 23 and 22.

Thus, since the impurity concentration at portions of the regions 1 and 2 forming the junction $J_e$ is selected low, the hole diffusion length $L_p$ at this portion is large. When the built-in-field at the potential barrier 7 is sufficiently large in magnitude, the diffusion length $J_p$ is expressed as follows:

$$J_p \approx \frac{qD_p P_n W_E}{L_p^2}(e^{\frac{qV}{kT}} - 1) \quad (12)$$

where $D_p$ is diffusion constant of holes in the emitter and $P_n$ is hole density in the emitter at equilibrium. The equation (12) reveals that the value of $J_p$ is reduced by a ratio of $W_E/L_p$ as compared with a case of no potential barrier.

An example of a transistor having a potential barrier in its emitter, using a hetero junction except the example using the L-H junction shown in FIG. 3. In other words, an N-type emitter region with large $L_p$ is provided adjacent to a P-type base region and a wide bandgap region is provided between the emitter region and the substrate surface to form a hetero junction. At this hetero junction, a potential barrier for holes is formed in the balance band.

The emitter region is composed of a semiconductor in which the width of bandgap is not narrower than that of the base region.

The wide bandgap region is formed by an N-type semiconductor region in opposition to the emitter junction between the emitter and base regions so as to have a shape such as preventing holes from being recombined at the semiconductor surface. In this case, the emitter injection efficiency can be further enhanced by providing in the conduction band a potential barrier such as to accelerate electrons. The height of the potential barrier for holes at the hetero junction is desired to be more than 0.1eV.

An idea using the hetero junction in a transistor is disclosed in, for example, Proc. IRE, vol. 45, p1535 (1957) in which a transistor as formed in therein an emitter-base junction. However, it was difficult to form a good hetero junction between P-type and N-type semiconductor regions.

Another embodiment of this invention using the hetero junction is shown in FIG. 4. On an N$^+$-type collector substrate 41 in which galium arsenide GaAs is doped with tin Sn at high concentration, an N$^-$-type semiconductor layer 42 of GaAs mainly forming a collector region 34 is formed by liquid epitaxial growth. Then, this layer 42 is partially doped with germanium Ge to form a P-type base region 33. However, the base region 33 may be formed with an epitaxial layer of GaAs. On the base region 33 there are respectively formed by liquid epitaxial growth an N$^-$-type semiconductor layer 43 of GaAs serving mainly as the emitter region 32 and an N-type semiconductor layer 44 of Ga$_{1-x}$Al$_x$As doped with Sn which mainly forms a wide bandgap emitter region 31 and consists of a different kind of material from that of the semiconductor layer 43. Germanium Ge is diffused through the semiconductor layers 43 and 44 so as to reach the base region 33 to form a P-type base contact layer 45. On the region 31 of the semiconductor layer 44 and on the substrate 41 there are respectively formed an emitter electrode 36e and a collector electrode 36c by Au-Ge alloy, and on the base contact layer 45 there is formed a base electrode 36b by Au-Zn alloy.

According to the above described construction, in addition to the formation of a good hetero junction 35 in the emitter, the hetero junction in the base contact layer 45 blocks electrons to improve its base transport efficiency and noise characteristics, and further the hetero junction between the layers 43 and 44, which are applied with the collector potential, reduces the surface recombination of electrons to improve its current characteristics and noise characteristics.

As described above, with the present invention, the potential barrier 7 as shown in FIG. 3 is provided in the emitter region or the first region 1 opposite to the emitter junction $J_e$ with a distance therebetween smaller than the hole diffusion length $L_p$, thereby to reduce the current density $J_p$ and, as apparent from the equation (9), to reduce the conductance component $g_p$. Particularly, in this invention, the following relation is established:

$$g_p < 10\, g_n \quad 13.$$

That is, the base operation of the base region 2A is cancelled while only the region 2 is utilized as the base operative region, thus the base transport efficiency $\beta$ is enhanced. Accordingly, the conductance component $g_n$ is decreased because the electron recombination in the region 2 is decreased. However, when $g_p$ is larger than $g_n$, the conductance $g_\pi$ is determined by $g_p$. For this reason, in the present invention, the values of the conductance components $g_p$ and $g_n$ are selected to satisfy the relation $g_p < 10 g_n$. As a result, the value of $g_\pi$ is made quite small as compared with the prior art. If $g_n$ is made as a reference, it is desired to decrease $g_p$ to an extent substantially the same as $g_n$. In order to make $g_p$ quite small, the built-in-field at the potential barrier 7 is made quite large, for example, about $10^4$ V/cm. Accordingly, as apparent from the equation (7) the factor $h_{FE}$ can be substantially enhanced according to this invention.

However, practically in the higher frequency range, the term $s(C_\pi + C_\mu + C_{JE})$ of the equation (4) becomes effective to change the phase and hence the absolute value $|h_{fe}|$ is decreased. If the highest value of a cut-off frequency at which the value of $|h_{fe}|$ is decreased to $1/\sqrt{2}$ the highest value is taken as $f_T$ ($= \omega_T/2\pi$), the following equation is obtained:

$$\omega_T = \frac{g_\pi}{C_\pi + C_{JE}} \quad (14)$$

(In this case, $C_\mu$ can be neglected since it is normally small.) If $g_\pi$ is small, $\omega_T$ tends to be lowered.

In the present invention, though $g_\pi$ is made small in order to increase $h_{FE}$ as mentioned above, the term of capacitance in the equation (14) is made quite small thereby to enhance $\omega_T$ or the cut-off frequency $f_T$. In other words, with the construction of this invention, since the both regions forming the first junction or emitter junction $J_e$, that is, the first and second regions 1 and 2, particularly the first region 1 is selected low in concentration, $C_{JE}$ can be selected quite small.

On the other hand, $C_\pi$ will be considered. Now, $C_\pi$ is divided into a base stored component $C_{\pi B}$ and an emitter stored component $C_{\pi E}$. That is, the following equation is established:

$$C_\pi = C_{\pi B} + C_{\pi E} \qquad (15)$$

If minority carrier charges stored in the base and emitter are taken as $g_B$ and $g_E$, and the widths of the base and emitter (having large $L_p$) are taken as $W_B$ and $W_E$, respectively, the relationships thereamong are expressed as follows:

$$C_{\pi B} = \frac{dq_B}{dV} \cong \frac{W_B^2}{2D_n} g_m \qquad (16)$$

$$C_{\pi E} = \frac{dq_E}{dV} \cong \frac{W_E L_\nu}{D_\nu} g_m(1-\gamma) \qquad (17)$$

In this case, however, the assumption is given as follows:

$$L_n > W_B \text{ and } L_\nu > W_E$$

As will be obvious from these equations (16) and (17), $C_{\pi B}$ and $C_{\pi E}$, that is, $C_\pi$ can be made small by reducing the base width $W_B$ and the emitter width $W_E$. An idea to make $W_E$ small is described in the above mentioned U.S. Pat. No. 2,822,310. However, since $L_p$ is selected large in order to make $h_{FE}$ large, $C_{\pi E}$ can not be made sufficiently large (If $L_p < W_E$ is satisfied as in the normal case, $C_{\pi E}$ is small irrespective of $W_E$). In this invention, as mentioned above $g_p$ is made small thereby to introduce the following relation:

$$C_{\pi E} < C_{\pi B} \qquad (18)$$

That is, from the equations (9) and (17) the following relation can be established:

$$C_{\pi E} \cong \frac{W_E L_\nu}{D_\nu} g_p \qquad (19)$$

As a result, it is noticed that if $g_p$ is made small, $C_{\pi E}$ can be made smaller than $C_{\pi B}$.

As described above, in the present invention, the equations (13) and (18) are satisfied thereby to provide a circuit wherein the cut-off frequency $f_T$ is high and $h_{fe}$ is high in the middle and high frequency ranges.

In the above described embodiments, the NPN-type transistor is mainly employed, but it will be understood that the PNP-type transistor can also be used by selecting the respective regions to have the reverse conductivity types to those of the illustrated regions.

An emitter-grounded type circuit using the aforementioned transistor is shown in FIG. 5. In FIG. 5, reference character $R_g$ represents a signal source impedance and Z denotes a collector load. In this invention, excepting the normal voltage during operation, the current driving operation can also be performed by making $R_g$ large because of high input impedance of the transistor.

It will be apparent that a number of changes and variations can be effected without departing from the scope of the novel concepts of the present invention.

We claim as our invention:

1. A circuit comprising:
   a transistor having a first region of semiconductor material of one conductivity type, a second region of semiconductor material of the opposite conductivity type interfaced with said first region and forming a first PN junction at the interface, a third region of semiconductor material of said one conductivity type interfaced with said second region on the opposite side thereof from said first region and forming a second PN junction at said second interface;
   an input circuit connected to said first and second regions;
   an output circuit connected to said first and third regions;
   the conductance of said first and second regions having first and second conductance components which correspond to the recombination of minority carriers in said first and second regions respectively;
   said conductance component in said first region being less than ten times the conductance component in said second region;
   and the capacitance caused by stored minority carriers in said first region being smaller than that in said second region.

2. A circuit according to claim 1, in which said first region of said transistor is provided therein with a third junction between a region of low impurity concentration and a region of high impurity concentration, which junction is spaced from said second region by a distance smaller than the diffusion length of minority carriers in said first region when said first junction is forwardly biased in operation, said region of low impurity concentration lying between said first and third junctions, and the width of said high impurity concentration region being less than the width of said low impurity concentration region.

3. A circuit according to claim 1, in which said first region is provided therein with a hetero junction spaced from said second region by a distance smaller than the diffusion length of minority carriers injected into said first region from said second region when said first junction is forwardly biased.

4. A circuit according to claim 2, in which the width of said high impurity concentration region is approximately one-half that of said low impurity concentration region.

5. A circuit according to claim 1, in which said second region is provided therein with a low impurity concentration portion and a high impurity concentration portion surrounding said low impurity concentration portion.

* * * * *